(12) United States Patent
Verhoeven et al.

(10) Patent No.: US 11,173,249 B2
(45) Date of Patent: Nov. 16, 2021

(54) SYRINGE (71) Applicant: VLOW Medical B.V., Eindhoven (NL)

(72) Inventors: Franciscus Maria Verhoeven, Amsterdam (NL); Andreas Adrianus Lambertus Van Den Houdt, Breda (NL); Paul Herman Maria Pessers, Arnhem (NL)

(73) Assignee: VLOW MEDICAL B.V., Eindhoven (NL)

( * ) Notice: Subject to any disclaimer, the term of this patent is extended or adjusted under 35 U.S.C. 154(b) by 0 days.

(21) Appl. No.: 16/087,871

(22) PCT Filed: Mar. 24, 2017

(86) PCT No.: PCT/NL2017/050187
§ 371 (c)(1),
(2) Date: Sep. 24, 2018

(87) PCT Pub. No.: WO2017/164743
PCT Pub. Date: Sep. 28, 2017

(65) Prior Publication Data
US 2019/0111211 A1    Apr. 18, 2019

(30) Foreign Application Priority Data
Mar. 24, 2016  (NL) ...................................... 2016494

(51) Int. Cl.
*A61M 5/315*   (2006.01)
*A61M 5/31*    (2006.01)

(52) U.S. Cl.
CPC ...... *A61M 5/31505* (2013.01); *A61M 5/3137* (2013.01); *A61M 5/31581* (2013.01);
(Continued)

(58) Field of Classification Search
CPC .... A61M 2005/31508; A61M 5/31581; A61M 5/31595; A61M 5/31525; A61M 5/31526; A61M 5/31528; A61M 5/31576
See application file for complete search history.

(56) References Cited

U.S. PATENT DOCUMENTS 2,409,656 A    10/1946  Austin
2,502,639 A *   4/1950  Blake ................ A61M 5/31595
                                                    604/210
(Continued)

FOREIGN PATENT DOCUMENTS

EP    2821089 A1    1/2015
EP    2821089 A1    7/2015
(Continued)

OTHER PUBLICATIONS

International Search Report PCT/NL2017/050187 dated Jul. 5, 2017.

*Primary Examiner* — Deanna K Hall
(74) *Attorney, Agent, or Firm* — Pillsbury Winthrop Shaw Pittman, LLP (57) ABSTRACT

The disclosure relates to a syringe, comprising a barrel and a plunger, wherein at least a part of said plunger is longitudinally slidably received in the barrel, wherein the plunger comprises a portion that is provided with at least one series of interspaced plunger formations, wherein the barrel is provided with a corresponding barrel formation for consecutively engaging successive ones of the plunger formations, wherein the syringe is arranged such as to be brought from a first state in which the barrel formation successively engages the plunger formations during slidable displacement of the plunger within the barrel, into a second state in which the barrel formation is held in a position spaced away from the plunger portion that comprises the plunger formations.

27 Claims, 10 Drawing Sheets

(52) U.S. Cl.
CPC . *A61M 5/31595* (2013.01); *A61M 2005/3126* (2013.01); *A61M 2005/31508* (2013.01)

(56) References Cited

U.S. PATENT DOCUMENTS 4,466,426 A    8/1984   Blackman
6,579,269 B1   6/2003   Kleyman

FOREIGN PATENT DOCUMENTS

| | | |
|---|---|---|
| FR | 1186571 A | 8/1959 |
| FR | 2535206 A1 | 5/1984 |
| WO | 2014/120795 A1 | 8/2014 |

* cited by examiner

SYRINGE

CROSS-REFERENCE TO RELATED APPLICATIONS

This is the U.S. National Stage of PCT/NL2017/050187, filed Mar. 24, 2017, which in turn claims priority to: Netherlands Application No. 2016494, filed Mar. 24, 2016, the contents of each of these applications being incorporated herein by reference in their entireties.

The invention relates to a syringe, especially a hypodermic syringe, wherein the syringe is suitable for, inter alia, the injection of fluids in medical applications, and the dosing of chemicals in non-medical applications, wherein the syringe comprises a barrel and a plunger of which at least a part is longitudinally slidably received in the barrel, and wherein the plunger comprises a portion that is provided with at least one series of interspaced plunger formations, that can for instance be formed by indents recessed in the plunger, wherein the barrel is provided with a corresponding barrel formation for consecutively engaging successive ones of the plunger formations.

Such syringes are for instance known from U.S. Pat. Nos. 6,579,269, 4,466,426 and EP 2 821 089. Such syringes can be advantageous over conventional syringes that are free of such plunger formations and such barrel formation. For example, during slidable displacement of the plunger within the barrel, e.g. while taking in a fluid or while expelling a fluid, engagement of the formation of the barrel and a respective one of the successive formations of the plunger may be perceived as a "click", which may provide audible and/or tactile feedback for instance with respect to dose-wise or unit-wise progress.

An indication of the dose-wise or unit-wise progress can for instance be highly advantageous in cases where the contents of the syringe is not to be expelled at once. This can for instance be the case in case of botulinum toxin injections, such as injections with botulinum toxin type A, which is popularly known by one of its tradenames: Botox, which is a protein and neurotoxin that is used in various cosmetic and medical procedures. In cosmetic applications, a botulinum toxin injection may be used to prevent the development of wrinkles by paralyzing facial muscles. In non-cosmetic applications, botulinum toxin may be used to treat conditions of excessive and inappropriate muscle contraction, spasticity (persistent states of muscle contraction), sphincter contraction, eye-movement disorders, tics and tremors. For instance because a treatment with botulinum toxin may typically include multiple injections at various sites of a body region to be treated, a dose-wise or unit-wise progress may be highly advantageous over conventional syringes not having a barrel formation and cooperating plunger formations. For example, the audible and/or tactile feedback provided by the coopering formations may allow a user, e.g. clinician, to focus his or her attention on the patient instead of on the syringe during administration of the fluid.

Nevertheless, known syringes comprising such a barrel formation and cooperating plunger formations also have disadvantages.

For example, especially in cases in which the cooperating formations are formed such as to provide a kind of "suck back" action during use in order to counteract that a drop may unintentionally be expelled after administering a desired dose or unit, for instance by forming said cooperating formations more or less in a ratchet-like manner and/or more or less such as disclosed in EP 2 821 089 with respect to the embodiment relating to its FIG. 5, it can be hard, if not almost impossible, to pull the plunger backwards in order to suck up fluid into the barrel of the syringe. Extra force and/or effort, needed to pull back the plunger, may be detrimental to the precision of the actions of the user. Hence, a user may take in too much fluid into the syringe. This may for example lead to waste, which can cause concern, for instance in terms of economical costs, e.g. in case of relatively expensive substances, such as relatively expensive medicaments or chemicals, or for instance in terms of environmental impact, e.g. in case of highly polluting and/or relatively toxic substances. Additionally or alternatively, the reduced precision may lead to other problems. For example, sucking up a liquid from a container, e.g. prior to injecting said liquid, a user may unintentionally lift the tip of a needle attached to the syringe out of said liquid to be sucked up and may then unintentionally suck up air or an other gas.

It is an object of the present disclosure to provide an alternative syringe. In particular, it can be an object of the disclosure to provide a syringe, wherein at least one of the disadvantages of a prior art syringe that comprises a barrel formation and which further comprises cooperating plunger formations is counteracted. More in particular, the disclosure may aim to provide a syringe wherein at least one of the disadvantages mentioned above is counteracted. In embodiments, the disclosure aims at providing a syringe comprising a barrel formation and cooperating plunger formations, which can counteract waste of substances to be administered by said syringe and/or which may counteract that errors occur during filling the barrel.

Thereto, the disclosure provides for a syringe, comprising a barrel and a plunger, wherein at least a part of said plunger is longitudinally slidably received in the barrel, wherein the plunger comprises a portion that is provided with at least one series of interspaced plunger formations, wherein the barrel is provided with a corresponding barrel formation for consecutively engaging successive ones of the plunger formations, wherein the syringe is arranged such as to be brought from a first state in which the barrel formation successively engages the plunger formations during slidable displacement of the plunger within the barrel, into a second state in which the barrel formation is held in a position spaced away from the plunger portion that comprises the plunger formations.

By arranging the syringe such that it can be brought from said first state into said second state, on the one hand audible and/or tactile feedback can be provided during expelling a fluid from the syringe by means of a more or less ratchet-like construction, while on the other hand it can be prevented that the more or less ratchet-like construction hinders taking in a fluid. Disengaging the barrel formation from the plunger portion provided with the plunger formations is an elegant solution that also enables controlled and easy refilling of the syringe, which for instance may not be possible in case a prefilled syringe would be provided that comprises a barrel formation and cooperating plunger formations for providing feedback during administering, but which does not allow to disengage said coopering formations. Besides, in such a less elegant solution, multiple prefilled syringes with different amounts of fluid need to be available in order to counteract wasting or spoiling of said fluid.

By biasing the barrel formation towards the plunger portion with the plunger formations, the barrel formation can be pressed against the plunger portion that is provided with the plunger formations in the first state of the syringe. For example, the syringe may thereto comprise a resilient part, such as a resilient finger, that is provided with the barrel formulation. Alternatively or additionally, a separate resilient element, such as a spring, may be provided to bias the barrel formation towards or away from said plunger portion.

Preferably, especially in embodiments in which the barrel formation is biased towards the plunger portion that is provided with the plunger formations, the syringe may comprise a switch, e.g. in order to bring the syringe from the first state into the second state of said syringe. Said switch may for instance be arranged to move said barrel formation away from said plunger portion with the plunger formations and/or to hold it temporarily away from said plunger portion.

Additionally or alternatively, the part of the plunger that is longitudinally slidably received in the barrel can further be rotatably arranged within the barrel, such that it can be rotated about a central axis of said plunger between at least two rotational positions of said plunger. This can be advantageous for different reasons.

For example, the rotatable plunger part can form a graduation portion providing for at least two mutually different, visually readable graduations that are alternatively selectable. The different graduations may then for instance have units of graduation or graduation increments that correspond to different commonly used mixture ratios or volume units, for example different commonly used mixture or dilution ratios or volume units used by manufactures of botulinum toxin, such as mixture or dilution ratios of 1 unit per 0.01 ml, 1 unit per 0.02 ml, 1 unit per 0.025 ml, 1 unit per 0.04 ml or 1 unit per 0.05 ml. Since volume units of 0.01 ml, 0.02 ml, 0.025 ml, 0.04 ml and 0.05 ml are currently compatible with most botulinum toxin brands that are approved for sale in for instance the US and the EU, a plunger having a graduation portion providing for multiple, e.g. two, three or four, graduations having a unit of graduation or graduation increment of respectively 0.01 ml, 0.02 ml, 0.025 ml, 0.04 ml and 0.05 ml conveniently allows a single syringe to be used in multiple of the accepted botulinum toxin treatments. For example, the graduation portion can provide for three graduations having graduation increments of respectively 0.01 ml, 0.02 ml and 0.04 ml. As another preferred example, the graduation portion can provide for three graduations having graduation increments of respectively 0.025 ml, 0.04 ml and 0.05 ml.

Advantageously, one or more, preferably each of the mutually different, visually readable graduations can correspond to a respective series of interspaced plunger formations. The interspace of the plunger formations, or so-called increment formations, of the respective series can correspond to the respective graduation. The longitudinal distance between two longitudinally adjacent increment formations of a respective series can then thus correspond to the graduation increment of the associated graduation, or at least to an integer multiple or integer fraction thereof.

Another example why it can be an advantage that the part of the plunger that is longitudinally slidably received in the barrel can also be rotatably arranged within the barrel between at least two rotational positions of said plunger may lie in that for instance a different starting point or starting time can be selected in case the plunger is provided with different time ordered sequences of indicia that have different starting points. This can for instance be advantageously in case a person requires a regular dose of an injectable medicine, for example a daily insulin injection. The time ordered sequence of indicia can then namely help a user to keep a track of when the last dose was taken or when the next dose is to be taken.

In embodiments, the plunger portion that is provided with the plunger formations, e.g. the graduation portion, can have a non-circular cross-section providing at least one guided surface, and the barrel can be provided with a guiding element comprising at least one guiding surface for guiding the guided surface of the plunger portion with the plunger formations during slidable displacement of the plunger within the barrel. By engaging at least a part of the non-circular cross-section of the plunger portion with the plunger formations, the guiding surface can then counteract that said portion unintentionally rotates. It will be appreciated that this can be highly advantageously, e.g. in order to prevent a person from unintentionally administering too much or too less.

Advantageous embodiments according to the disclosure are described in the appended claims.

By way of non-limiting examples only, embodiments of the present disclosure will now be described with reference to the accompanying figures in which.

It is noted that the figures show merely preferred embodiments according to the disclosure. In the figures, the same or similar reference signs or numbers refer to equal or corresponding parts.

FIGS. 1A-1E show schematic top, side, bottom, front and rear views, respectively, of a first embodiment of a syringe 1, which for example can be a hypodermic syringe for administering of medical liquids, such as for instance a botulinum toxin. For example, the syringe 1 can be arranged for subcutaneous or intravenous injections. Here, the syringe 1 comprises an elongate barrel 2 and an elongate plunger 3. At least a part 30 of said plunger 3 is coaxially slidably received in the barrel 2. Both barrel 2 and plunger 3 may for instance be made from plastic, for example through injection molding.

Figure 5A:
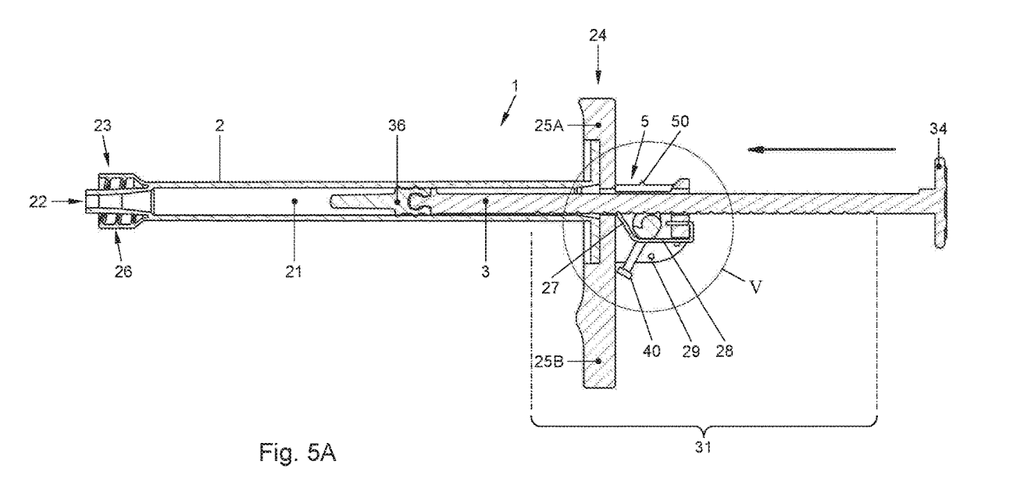
FIG. 5A shows a schematic cross-sectional view of a second embodiment of a syringe according to an aspect of the disclosure in a first state of said syringe.
Figure 6A:
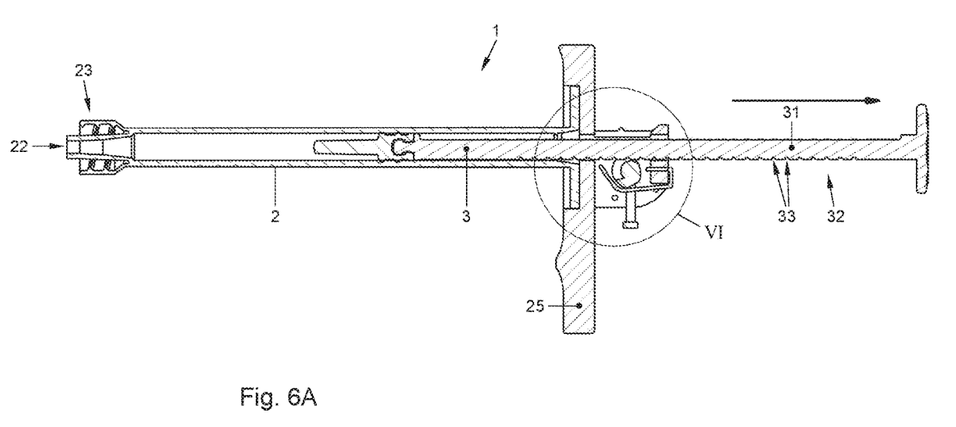
FIG. 6A shows a schematic cross-sectional view of the syringe of FIGS. 5A-5B in a second state of said syringe.
Figure 7A:
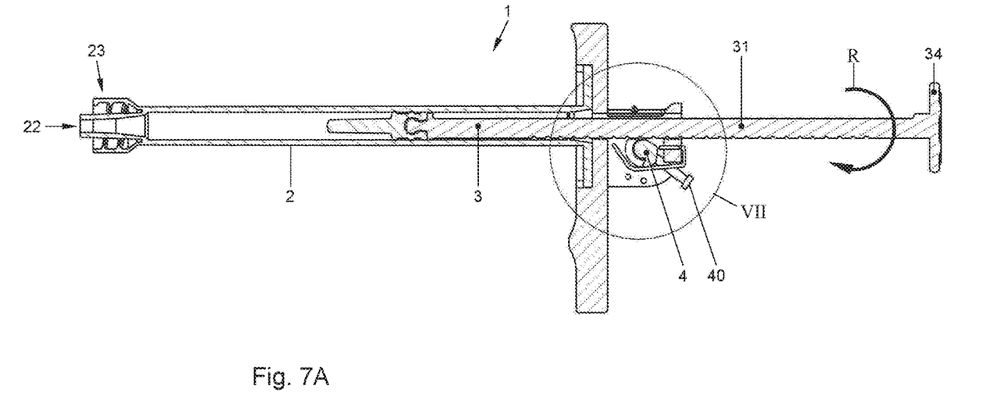
FIG. 7A shows a schematic cross-sectional view of the syringe of FIGS. 5A-6B in a third state of said syringe.

The barrel 2 may include an elongate tubular, e.g. round cylindrical formed, body 20 that extends along a longitudinal axis A1 of the syringe 1. As best can be seen in FIGS. 5A, 6A and 7A, which show an alternative embodiment of the syringe 1 in three different states of said syringe 1, the barrel 2 defines a central bore 21 for containing a fluid, e.g. a liquid or gas. In said central bore 21, the plunger 3 can be longitudinally slidably received. The plunger 3 can be movable along the longitudinal direction of the barrel 2 to allow the syringe 1 to take in a fluid or to expel a fluid, respectively, through a fluid port 22 or opening located at a distal end 23 of the barrel 2. It will be appreciated that the plunger 3, especially a distal end thereof, may be provided with a sealing element or sealing member 36. The sealing element 36, which may be made of a suitably flexible and/or fluid impermeable material, may be dimensioned to enable slidable, sealing contact with an inner wall of the central bore 21 of the barrel 2 and the fluid port 22 located at a distal end 23 of the barrel 2.

At a proximal end region 24, the barrel 2 may be provided with a grip 25, which for instance may be formed as one or multiple finger wings 25A, 25B. The grip 25 may facilitate a user to press an extended plunger 3 into the bore 21 of the barrel 2, e.g. by pressing a handle 34 of the plunger 3 with a thumb, while supporting two fingers, e.g. an index finger and a middle finger, distally against the finger wings 25A, 25B in a conventional manner of syringe operation.

The barrel 2 may be provided with a needle attachment 26, which for instance may be formed by a hollow tip provided at the distal end of the barrel 2. The needle attachment 26 may be of any suitable type, e.g. a Luer-Slip tip or a Luer-Lock tip.

Figure 1A:
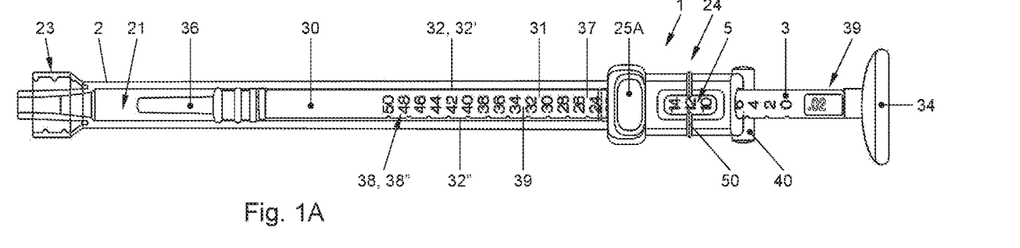
FIGS. 1A-1E show schematic top, side, bottom, front and rear views, respectively, of a first embodiment of a syringe according to an aspect of the disclosure.
Figure 1B:
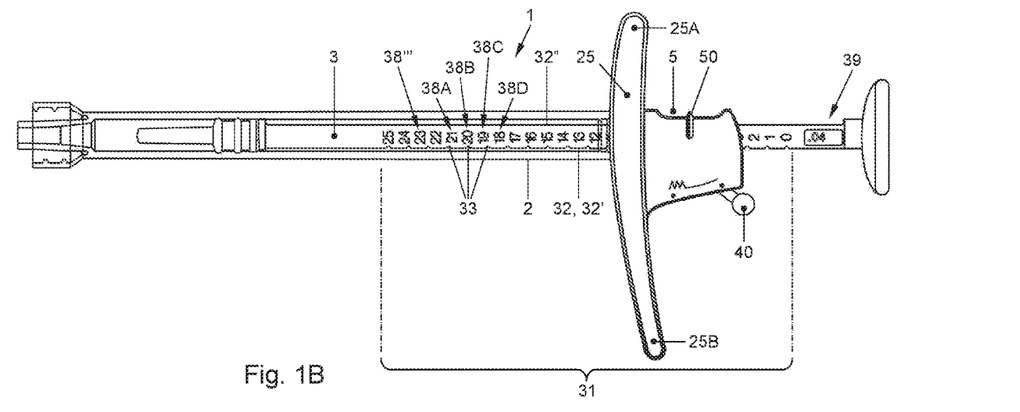
Figure 1C:
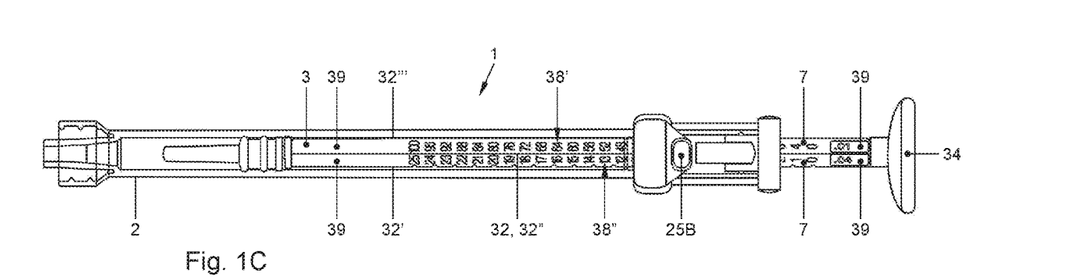
Figure 1D:
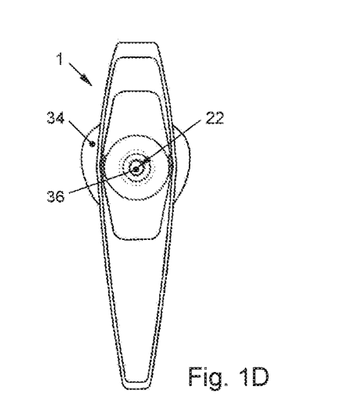
Figure 1E:
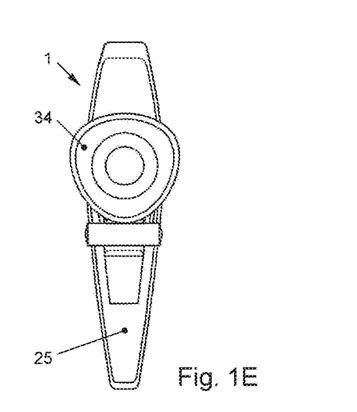
Figure 2:
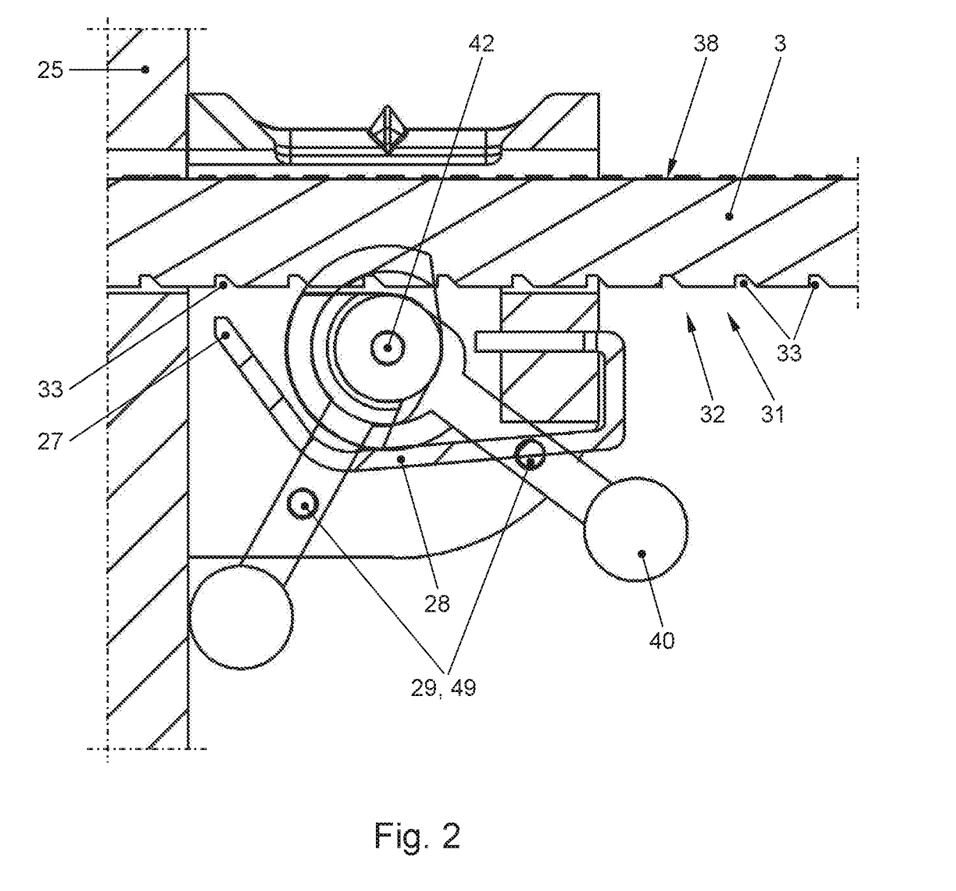
FIG. 2 shows a schematic cross-sectional view of the syringe of FIGS. 1A-1E.

As for instance can be seen in FIG. 1B and the cross-sectional view of FIG. 2, the plunger 3 comprises a portion 31 that is provided with at least one series 32 of interspaced plunger formations 33 or so-called plunger structures 33. Preferably, the plunger formations 33, which may form increment formations 33, can be equidistantly spaced from one another.

The barrel 2 is provided with a barrel formation 27 for consecutively engaging successive ones of the plunger formations 33 when the plunger 3 slides through the barrel 2, e.g. during administration of a fluid, preferably a liquid, especially a medicine. During such sliding action, each engagement of the formation 27 of the barrel 2 and a respective one of the successive formations 33 of the plunger 3 may cause a variation in the resistance to the slidable displacement of the plunger 3, e.g. an temporal increase in resistance. Such engagements may be in the form of a snap and/or may be perceived as a "click". Additionally or alternatively, each of a series of successive engagements may provide audible and/or tactile feedback that can inform a user of unit-wise progress during the administration of an injection. This may for instance be advantageous when only a single unit has to be injected, but may for instance also be advantageous for metering when a predetermined multiple number of units has to be injected.

Although the plunger formations 33 are here formed by indents 33 recessed in the plunger 3, which are to be engaged by a barrel formation 27 formed by a protrusion, said plunger and/or barrel formations 33, 27 or structures 33, 27 may be formed differently in alternative embodiments. For example, the plunger formations 33 may be formed as protrusions, which may for instance extend substantially radially away from the portion 31 that is provided with said at least one series 32 of interspaced plunger formations 33. For example due to that the sealing member 36 may be wider than said plunger portion 31, such plunger portion 31 may be slidable in the bore 21 even if it is provided with such protruding plunger formations. In case of protruding plunger formations, the barrel formation may for instance be formed by means of an indent in a barrel member that can be biased towards said plunger portion 31. However, in case of protruding plunger formations, the barrel formation may alternatively be formed by means of a protrusion for engaging the protruding plunger formations during sliding motion of the plunger 3, e.g. when sliding said plunger towards the distal end 23 of the barrel 2.

Figure 5B:
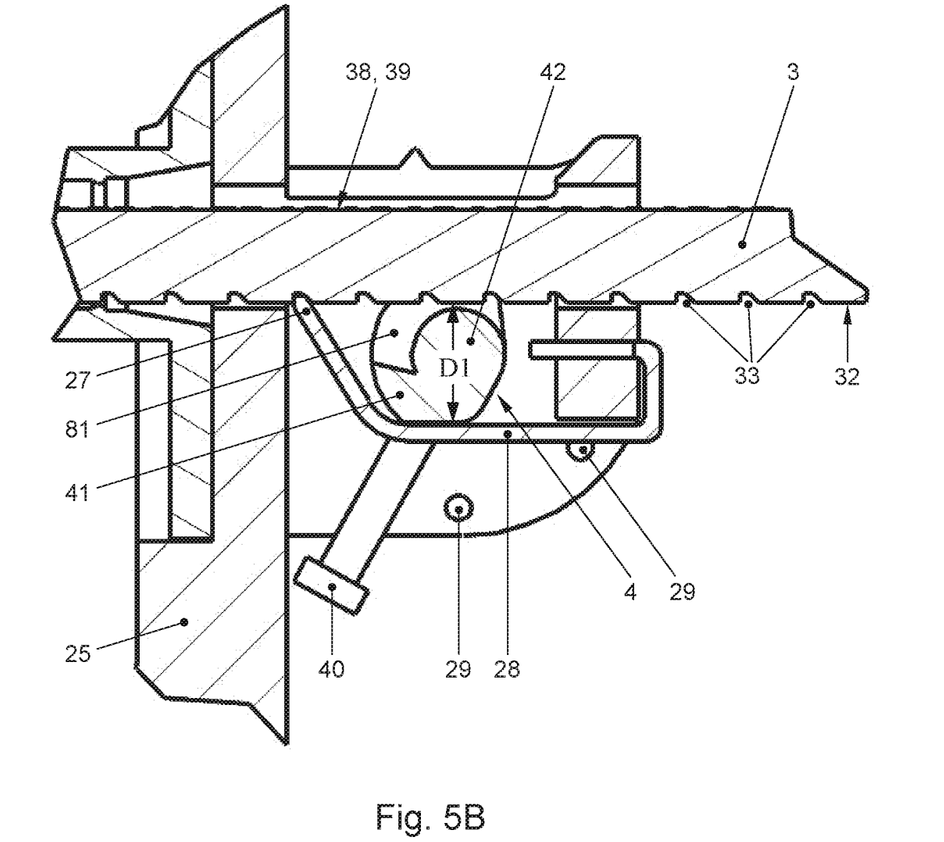
FIG. 5B shows a schematic detail of the cross-sectional view of FIG. 5A.
Figure 6B:
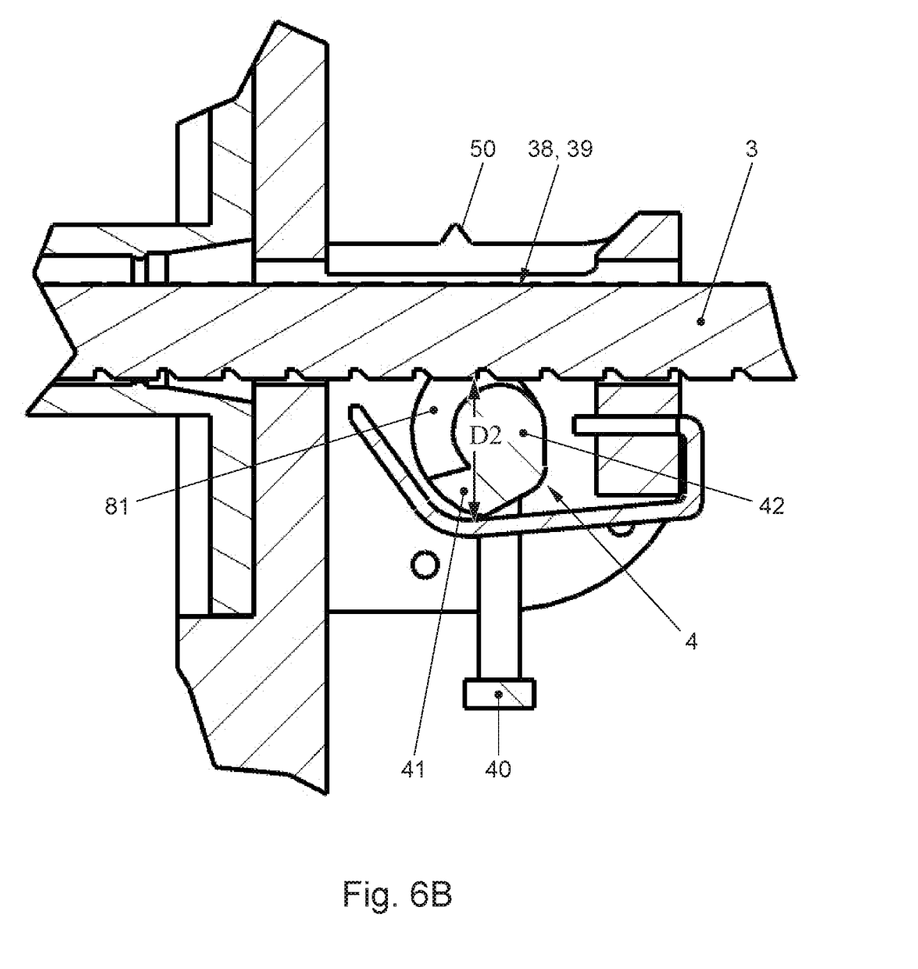
FIG. 6B shows a schematic detail of the cross-sectional view of FIG. 6A.

As may be understood from FIG. 2 or from FIGS. 5B and 6B, which all show schematic details of cross-sections of embodiments of the syringe 1, the syringe 1 is arranged such as to be brought from a first state (see e.g. FIGS. 5A and 5B) in which first state the barrel formation 27 successively engages the plunger formations 33 during slidable displacement of the plunger 3 within the barrel 2, into a second state (see e.g. FIGS. 6A and 6B) in which the barrel formation 27 is held in a position spaced away from the plunger portion 31 that comprises the plunger formations 33.

By arranging the syringe 1 such that it can be brought from said first state into said second state, on the one hand audible and/or tactile feedback can be provided during expelling a fluid from the syringe by means of a more or less ratchet-like construction, while on the other hand it can be prevented that the more or less ratchet-like construction hinders taking in a fluid.

Preferably, the barrel formation 27 can be biased towards the plunger portion 31 with the plunger formations 33. As a result, in the first state (see e.g. FIGS. 5A and 5B), the barrel formation 27 can be pressed against said plunger portion 31 with the plunger formations 33. For example, the syringe 1 may comprise a resilient part 28, such as a resilient finger, that is provided with the barrel formation 27 and which is arranged to bias said barrel formation 27, which may be formed by a distal end portion of said resilient part 28, towards the plunger portion 31 that is provided with the series 32 of plunger formations 33. Alternatively or additionally, a separate resilient element, such as a spring, may be provided to bias the barrel formation 27.

In preferred embodiments, the syringe 1 may comprise a switch 4 to bring the syringe 1 from the first state (see e.g. FIG. 5B) into the second state (see e.g. FIG. 6B) and/or vice versa. Said switch 4, which may comprise a switch handle 40 for manually operating said switch 4, can comprise a pushing member 41 for pushing the barrel formation 27 away from the plunger portion 31 that is provided with the plunger formations 33. Alternatively or additionally, the pushing member may be for pushing the barrel formation 27 towards said plunger portion 31 comprising the plunger formations 33, e.g. in cases the barrel formation 27 is biased away from said plunger portion or in case the barrel formation 27 is not biased, respectively.

Advantageously, the syringe 1 is arranged such that the switch 4 can be moved from a first position (see e.g. FIGS. 2 and 5B) that corresponds to the first state of the syringe to a second position (see e.g. FIGS. 2 and 5B) of said switch 4 that corresponds to the second state of the syringe 1, wherein in said first position of the switch 4 the pushing member 41 is located in a first position facilitating that the barrel formation 27 is positioned to be in contact with the plunger formations 33 during slidable displacement of the plunger 3, and wherein in the second position of the switch 4 the pushing member 41 is located in a second position facilitating that the barrel formation 27 is positioned away from the plunger portion 31 that is provided with the plunger formations 33.

Advantageously, the switch 4 can be rotatably attached to the barrel 2. In particular, a rotation axis 42 about which the switch 4 can be rotated may extend substantially transverse to the longitudinal direction of the plunger 3 and/or the direction in which the plunger 3 slides during use.

In cases the barrel formation 27 is biased towards the plunger 3, as is for example the case in the shown embodiments, the pushing member 41 may be moved further away from the plunger 3 when the switch 4 is brought from its first position corresponding to the first state of the syringe 1 to its second position corresponding to the second state of the syringe 1, for example compare the distance D2 in FIG. 6B with the distance D1 in FIG. 5B which is smaller than distance D2. Here, see e.g. FIG. 5B, the pushing member 41 is still in contact with the resilient part 28 provided with the barrel formation 27 when the switch 4 is brought from its second position into its first position. However, in alternative embodiments, the pushing member 41 may be spaced apart from the resilient part 28 provided with the barrel formation 27 in the first position of the switch 4.

With respect to the part 30 of the plunger 3 that is longitudinally slidably received in the barrel 2, it is noted that at least said part 30 of the plunger may be rotatable within the barrel 2 between at least two rotational positions of the plunger 3. For example, the rotatable plunger part 30 can form a graduation portion 37 providing for at least two mutually different, visually readable graduations 38 that are alternatively selectable. The alternatively selectable, mutually different, visually readable graduations 38', 38'', 38''' that can be provided by the rotatable plunger part 30 may for instance have units of graduation or graduation increments that correspond to different commonly used mixture ratios or volume units, for example different commonly used mixture or dilution ratios or volume units used by manufactures of botulinum toxin, such as mixture or dilution ratios of 1 unit per 0.01 ml, 1 unit per 0.02 ml, 1 unit per 0.025 ml, 1 unit per 0.04 ml or 1 unit per 0.05 ml. Advantageously, one or more, preferably each of the mutually different, visually readable graduations 38', 38'', 38''' can correspond to a respective series 32', 32'', 32''' of interspaced plunger formations 33. The interspace of the plunger formations, or so-called increment formations 33, of the respective series 32', 32'', 32''' can correspond to the respective visually readable graduation 38', 38'', 38'''. The longitudinal distance between two longitudinally adjacent increment formations 33 of a respective series 32', 32'', 32''' can then thus correspond to the graduation increment of the associated graduation, or at least to an integer multiple or integer fraction thereof. A series 32 of interspaced plunger formations 33 or so-called plunger structures 33, can preferably be uniformly spaced apart at an interval corresponding to a predetermined dose of fluid traversing a fluid port 22, passage or outflow opening formed in the barrel 2.

The graduation portion 37 may preferably comprise a longitudinally extending, generally prismatic body. Here 'generally prismatic' may be construed to refer to both truly prismatic bodies having planar faces/sides 39, and bodies that are only approximately prismatic, for instance because their faces 39 are slightly convexly or concavely curved and/or because their longitudinal edges/corners are rounded off. The prism reflected by the generally prismatic body may typically be a regular right prism. The graduation portion 37 of the plunger 3 can comprise a generally triangular prismatic body (having a generally triangular cross-section).

In case the graduation portion 37 has a generally prismatic shape, each of the graduations 38 may for example be exclusively associated with one of its longitudinally extending faces 39. Each graduation 38 may, for instance, be printed on one of these faces 39, as in the depicted embodiment of FIGS. 1A-1E.

In embodiments, the barrel 2 may define a reading window 5 through which a user can see the plunger 3, and more in particular a selected graduation 38 provided on the graduation portion 37 of the plunger 3, and, optionally, a volume unit indication 39 provided by a volume unit indication portion of the plunger 3. Structurally, the reading window 5 may be a suitably dimensioned aperture 5, in a wall of the barrel or in a collar of the barrel. Here, 'suitably dimensioned' means that the dimensions of the aperture may be tailored to the configuration of in particular the graduation portion 37 of the plunger 3, so that, when a certain graduation 38', 38'', 38''' is selected by rotation of the plunger 3 relative to the barrel 2, only that selected graduation 38 is visible through the reading window 5. In one embodiment, the edge or margin of the reading window 5 may be provided with an index 50, e.g. a notch, that may align with successive graduation marks 38A, 38B, 38C, 38D of a selected graduation 38 when the plunger 3 is slid into and out of the barrel 2 during use.

Although the plunger portion 31 with the plunger formations 33, which thus may form or comprise a graduation portion 37, may in embodiments be of substantially prismatic shape, said plunger portion 31 with the plunger formations 33 may be formed differently in alternative embodiments.

It is noted that said plunger portion 31 which is provided with the plunger formations 33 preferably can be shaped such as to have a non-circular cross-section. This may for instance be by means of a generally prismatic body of a different type, e.g. a tetragonal or pentagonal prismatic body, which then thus can have a generally tetragonal or pentagonal cross-section, respectively. Alternatively or additionally, the plunger portion 31 which is provided with the plunger formations 33 can comprise grooves or edges. Although the edges may for instance be formed by corners of a substantially prismatically shaped plunger portion that comprises the plunger formations, longitudinally extending indentations or protrusions may alternatively or additionally be provided in or on an outer surface of the plunger. Said longitudinally extending protrusions or indentations may be for guiding the plunger during longitudinal sliding and for counteracting rotational movement of said plunger within the barrel. For example, the plunger portion with the plunger formations may have a substantially circular cylindrical shape and may be provided with longitudinally extending grooves or edges, as a result of which the plunger portion with the plunger formations thus has a non-circular cross-section.

In cases in which the plunger portion 31 with the plunger formations 33 has a non-circular cross-section, said non-circular cross-section can provide at least one guided surface 7. Additionally, the barrel 2 can then be provided with a guiding element 8. Said guiding element 8 can be for engaging at least a part of the non-circular cross-section of the plunger portion 31 that is provided with the plunger formations 33 and for counteracting that said portion 31 unintentionally rotates. Said guiding element 8 may comprise at least one guiding surface 81 for guiding the guided surface 7 of the plunger portion 31 with the plunger formations 33 during slidable displacement of the plunger 3 within the barrel 2. Preferably, the guiding element 8 may comprise two guiding surfaces 81 for guiding two respective guided surfaces 7 of the plunger 3, preferably two substantially opposite guided surfaces or two facing guided surfaces. For example, in case of a substantially triangular prism shaped plunger portion 31, the two guiding surfaces 81 may for instance be facing each other and be tilted with respect to each other, such as for instance can be seen in FIG. 3, such that they can guide two substantially opposite guided surfaces 7 that are tilted with respect to each other.

In embodiments, the syringe 1 can be arranged such that in its first state the guiding element 8 is in a position such that one or more of its guiding surfaces 81 can guide one or more of the at least one guided surfaces 7, such as for instance can be seen in FIG. 5B. Since the barrel formation 27 is in the first state of the syringe 1 positioned such as to successively engage the plunger formations 33 during slidable displacement of the plunger 3 within the barrel 2, the first state of the syringe 1 can provide for controlled injection or administering as the cooperating formations 27, 33 can provide audible and/or tactile feedback and as (the one or more guiding surfaces 81 of) the guiding element 8 can counteract that the plunger 3 rotates accidentally.

Furthermore, the syringe 1 may additionally or alternatively be arranged such that in the second state the guiding element 8 is in a position such that at least one of its one or multiple guiding surfaces 81 can guide one or more of the at least one guided surfaces 7, as can be seen in FIG. 6B. As, in said second state of the syringe 1, the barrel formation 27 is held in a position spaced away from the plunger portion 31 that comprises the plunger formations 31, said second state can be used relatively well for sucking up a fluid into the syringe 1, because the cooperating formations 27, 33 are then not engaging. Moreover, this can then be done without unintentionally rotating the plunger 3, as the guiding element 8 can prevent the plunger from such rotation.

The syringe 1 may further be arranged to be brought into a third state (see FIGS. 7A and 7B) in which the barrel formation 27 is held away from the plunger portion 31 that is provided with the plunger formations 33 and the guiding element 8 is in a position releasing the guided surface 7. In said third state, the plunger 3 may thus be rotated, preferably even in a position in which the plunger 3 is slit relatively far or even maximally into the barrel 2. Since the barrel formation 27 is held away from the plunger portion 31 with the plunger formations 33, it also is counteracted that said barrel formation 27 hinders rotation. A free rotational movement R of the plunger 3 can thus be facilitated.

It is noted that, in alternative embodiments, such as for instance is the case with the embodiment of FIGS. 1A-1E and 2, the syringe 1 may be arranged such that in its second state the guiding element 8 is in a position in which it is not guiding the guided surface 7. In such embodiments, the syringe 1 may thus have two states (see FIG. 2), one state in which rotation of the plunger 3 is counteracted and the barrel formation 27 and the plunger formations 33 engage during sliding, and a second state in which rotation of the plunger 3 is not counteracted and in which the barrel formation 27 and the plunger formations 33 do not engage during sliding.

Although the switch 4 is here above described as to bring the syringe 1 from the first state (see e.g. FIG. 5B) into the second state (see e.g. FIG. 6B) and/or vice versa, it will be appreciated that the switch 4 can additionally or alternatively be arranged for bringing the syringe 1 from the first or second state (see e.g. FIGS. 5B and 6B, respectively) into the third state (see e.g. FIG. 7B) and/or vice versa.

Figure 3:
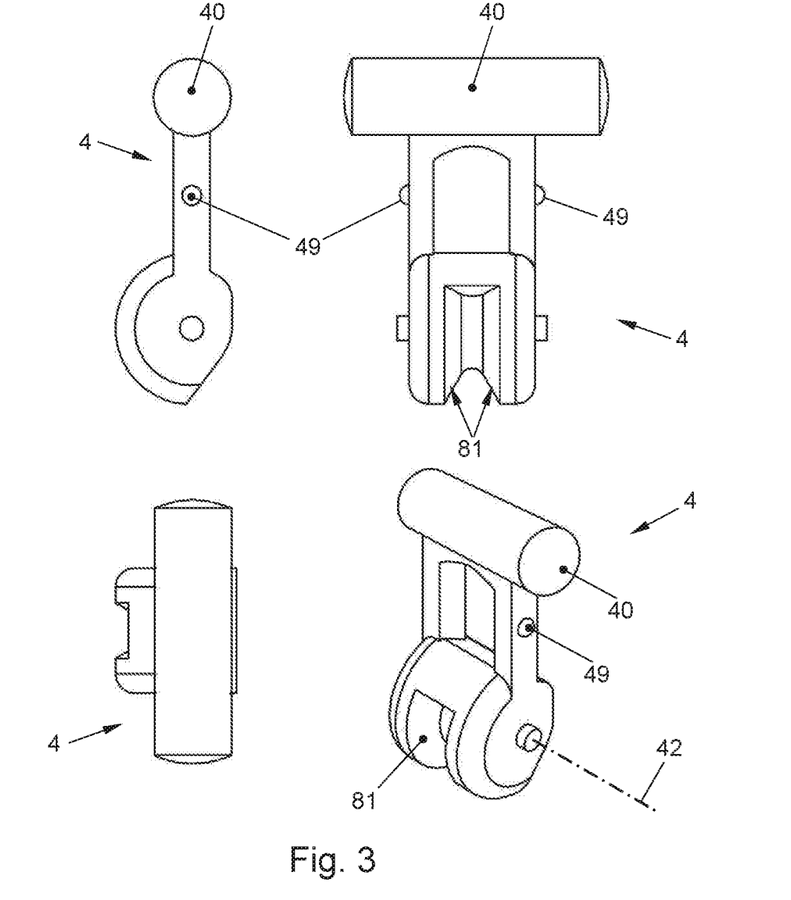
FIG. 3 shows schematic views of a switch of the syringe shown in FIGS. 1A-2.
Figure 4:
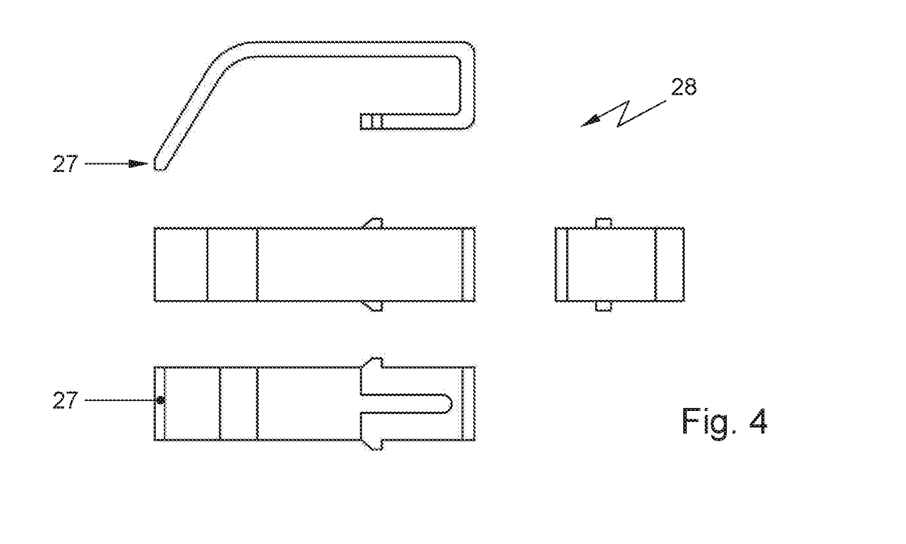
FIG. 4 shows schematic views of a part of the syringe shown in FIGS. 1A-2, which part forms a barrel formation.

As can for instance be seen in the exemplary embodiment of FIG. 3, the switch 4, which may comprise the pushing member 41, may also comprise the guiding element 8 that comprises the one or multiple guiding surfaces 81. In the first position of the switch 4, in which the pushing member 41 is located in a first position facilitating that the barrel formation 27 is positioned to be in contact with the plunger formations 33 during slidable displacement of the plunger 3, one or more of said one or more guiding surfaces 81 can be located in a first position in which it/they guide(s) one or more of the one or more guided surfaces 7 and counteract(s) rotation of the plunger portion 31 which is provided with the plunger formations 33.

In the second position of the switch 4, in which the pushing member 41 is located in a second position facilitating that the barrel formation 27 is positioned away from the plunger portion 31 having the plunger formations 33, the guiding surface(s) is/are moved towards a second position in which at least one guiding surface guides the guided surface 7.

Moreover, the syringe 1 can be arranged such that the switch 4 can be moved from the second position towards a third position corresponding with the third state of the syringe 1, wherein in the third position of the switch 4 the pushing member 41 is located in a third position facilitating that the barrel formation 27 is positioned away from the plunger portion 31 comprising the plunger formations 33, and in which the guiding surface 81 is located in a third position in which it released the guided surface 7.

Figure 7B:
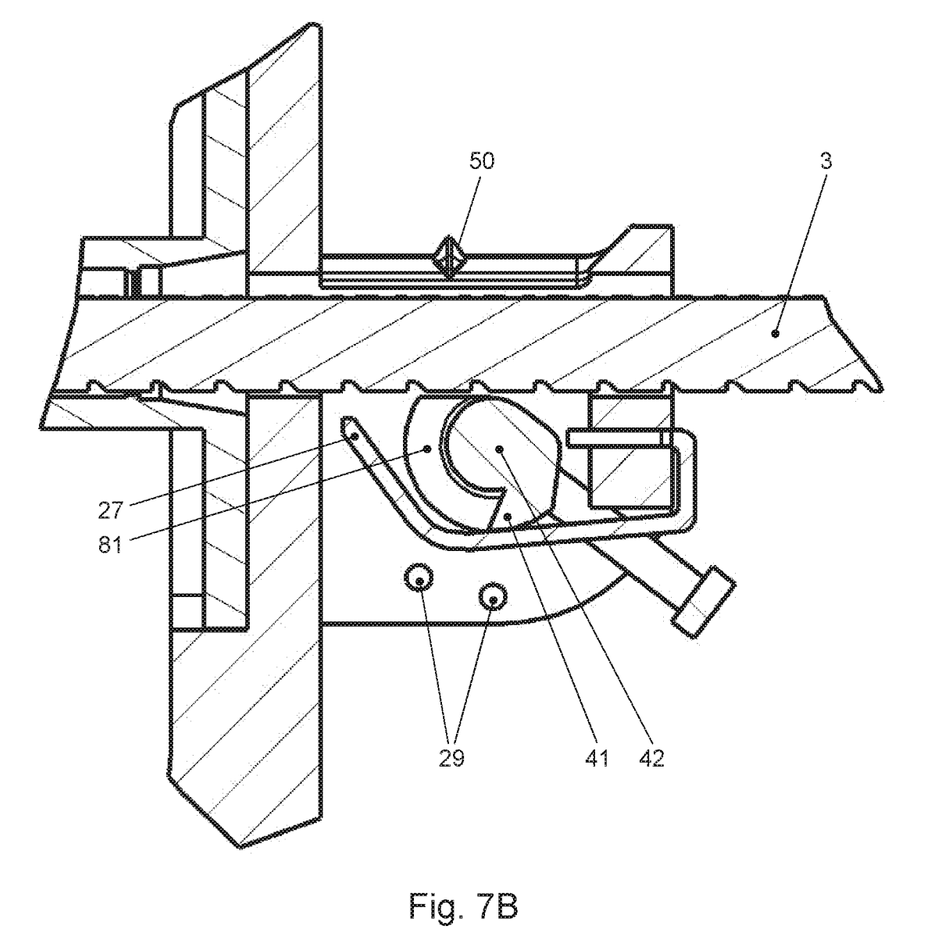
FIG. 7B shows a schematic detail of the cross-sectional view of FIG. 7A.

As for instance can be seen in FIGS. 5B, 6B and 7B, the switch 4 can be rotatably attached to the barrel 2, and a rotation axis 42 about which the switch 4 can be rotated may then extend substantially transverse to the longitudinal direction of the plunger 3. Then, one or multiple guiding surfaces 81 may extend over a part of an arc around said rotation axis 42 of the switch 4. Upon rotation of the switch 4 from its first position to its second position or vice versa, the guiding surface(s) 81 may rotate while they can keep guiding the plunger 3 without releasing it in between.

In preferred embodiments, the syringe 1 can be arranged to be held in its first state and/or can be arranged to be held in its second state and/or can be arranged to be held its third state. Thereto, the syringe 1 can for instance be arranged with a locking mechanism 29, 49 to hold the switch 4, which can be movable, e.g. rotatable, suspended with respect to the barrel 2, in one or more of its corresponding positions. The locking mechanism may include locking formations 29, 49 or locking structures 29, 49 that are provided by the barrel 2 and the switch 4, respectively, and that are configured to engage each other, for instance in a resilient snap type action, when the switch 4 is moved from one of its positions to an other one of its positions, so as to releasably lock the switch 4 in its respective position. The syringe 1 may thus comprise retainers 29, 49, e.g. formed by releasable snap means 29, 49, for holding the switch 4 in a respective position of said switch 4.

It is noted that for the purpose of clarity and a concise description, features are described herein as part of the same or separate embodiments, however, it will be appreciated that the scope of the disclosure may include embodiments having combinations of all or some of the features described.

Further, it is noted that the disclosure is not restricted to the embodiments described herein. It will be understood that many variants are possible.

Such variants will be apparent for the person skilled in the art and are considered to lie within the scope of the claimed invention as formulated in the following claims.

The invention claimed is:

1. A syringe, comprising a barrel and a plunger, at least a part of said plunger is longitudinally slidably received in the barrel, wherein the plunger comprises a portion that is provided with at least one series of interspaced plunger formations, wherein the barrel is provided with a corresponding barrel formation for consecutively engaging successive ones of the plunger formations, wherein the syringe is arranged such as to be brought from a first state in which the barrel formation successively engages multiple ones of the plunger formations during longitudinally sliding displacement of the plunger within the barrel in a longitudinal direction in which the plunger moves further into the barrel, into a second state in which the barrel formation is held in a position spaced away from the plunger portion that comprises the plunger formations, wherein the syringe is arranged such that, during said longitudinally sliding displacement of the plunger in said longitudinal direction in which the plunger moves further into the barrel, each of the engagements of the barrel formation and a respective one of the successive ones of the successive plunger formations causes a variation in the resistance to the sliding displacement of the plunger in said longitudinal direction further into the barrel.

2. The syringe according to claim 1, wherein the barrel formation is biased towards the plunger portion with the plunger formations.

3. The syringe according to claim 1, wherein the part of the plunger that is longitudinally slidably received in the barrel further is rotatable within the barrel between at least two rotational positions of the plunger.

4. The syringe of claim 3, wherein the plunger portion with the plunger formations has a non-circular cross-section providing at least one guided surface, and wherein the barrel is provided with a guiding element comprising at least one guiding surface for guiding the guided surface of the plunger portion with the plunger formations.

5. The syringe of claim 4, wherein the syringe is arranged such that in the first state the guiding element is in a position to guide the guided surface.

6. The syringe of claim 4, wherein the syringe is arranged such that in the second state the guiding element is in a position to guide the guided surface.

7. The syringe according to claim 4, wherein said syringe is further arranged to be brought into a third state in which the barrel formation is held away from the plunger portion with the plunger formations and the guiding element is in a position releasing the guided surface.

8. The syringe according to claim 4, comprising a switch to bring the syringe from the first state into the second state and/or vice versa, and/or to bring the syringe from the first or second state into the third state and/or vice versa.

9. The syringe according to claim 8, wherein the switch comprises the guiding element that comprises the guiding surface, said switch further comprising a pushing member for pushing the barrel formation away from the plunger portion with the plunger formations and/or pushing the barrel formation towards said plunger portion comprising the plunger formations.

10. The syringe according to claim 9, wherein the switch can be moved from a first position corresponding to the first state of the syringe to a second position corresponding to the second state of the syringe, wherein in the first position of the switch the pushing member is located in a first position facilitating that the barrel formation is positioned to be in contact with the plunger formations during slidable displacement of the plunger, and the guiding surface is located in a first position in which it guides the guided surface and counteracts rotation of the plunger portion with the plunger formations, and wherein in the second position of the switch the pushing member is located in a second position facilitating that the barrel formation is positioned away from the plunger portion with the plunger formations, and the guiding surface is moved towards a second position in which it also guides the guided surface.

11. The syringe according to claim 10, wherein the switch can be moved from the second position towards a third position corresponding with the third state of the syringe, wherein in the third position of the switch the pushing member is located in a third position facilitating that the barrel formation is positioned away from the plunger portion with the plunger formations, and in which the guiding surface is located in a third position in which it released the guided surface.

12. The syringe according to claim 9, wherein the switch is rotatably attached to the barrel.

13. The syringe according to claim 12, wherein a rotation axis about which the switch can be rotated extends substantially transverse to the longitudinal direction of the plunger, and wherein the guiding surface extends over a part of an arc around said rotation axis of the switch.

14. The syringe according to claim 7, wherein the syringe is arranged to be held in its first state and/or is arranged to be held in its second state and/or is arranged to be held in its third state.

15. The syringe according to claim 8, wherein the syringe comprises retainers, formed by releasable snap means, for holding the switch in a respective position of said switch.

16. A syringe according to claim 1, wherein in the second state the barrel formation is spaced apart from the plunger.

17. A syringe, comprising a barrel and a plunger, at least a part of said plunger is longitudinally slidably received in the barrel, wherein the plunger comprises a plunger portion that is provided with at least one series of interspaced plunger formations, wherein the barrel is provided with a corresponding barrel formation for consecutively engaging successive ones of the interspaced plunger formations, wherein the syringe is arranged such as to be brought from a first state in which the barrel formation successively engages the interspaced plunger formations during sliding displacement of the plunger within the barrel during administration of a fluid, such that during said sliding displacement during the administration of the fluid each engagement of the barrel formation and a respective one of the successive interspaced plunger formations causes a variation in the resistance to the sliding displacement of the plunger, into a second state in which the barrel formation is held in a position spaced away from the plunger portion that comprises the interspaced plunger formations.

18. The syringe according to claim 17, wherein the barrel formation and interspaced plunger formations are formed such that during movement of the plunger relative to the barrel for administration of the fluid the barrel formation can ratchet over said interspaced plunger formations in the first state.

19. The syringe according to claim 17, wherein in the first state the plunger is prevented from a continuous movement inside the barrel away from a distal end of the barrel during taking in of the fluid through a distal end of the syringe.

20. The syringe according to claim 17, wherein in the second state the barrel formation is spaced apart from the plunger portion comprising the interspaced plunger formations.

21. A syringe according to claim 17, wherein in the second state the barrel formation is spaced apart from the plunger.

22. A syringe, comprising a barrel and a plunger, at least a part of said plunger is received in the barrel, longitudinally slidable in a first direction from a proximal end of the barrel to a distal end of said barrel for dispensing a fluid from said syringe and in an opposite second direction for taking in fluid into said barrel, wherein the plunger comprises a portion that is provided with at least one series of interspaced plunger formations, wherein the barrel is provided with a corresponding barrel formation for consecutively engaging successive ones of the interspaced plunger formations, wherein the syringe is arranged such as to be brought from a first state in which the barrel formation successively engages the interspaced plunger formations during sliding displacement of the plunger within the barrel, into a second state in which the barrel formation is held in a position spaced away from the plunger portion that comprises the interspaced plunger formations, wherein the plunger in the first state is movable in the first direction with the barrel formation ratcheting over the interspaced plunger formations, but is prevented from continuous movement in the second direction by said barrel formation and at least one of said interspaced plunger formations, and in the second state is movable at least in the second direction continuously.

23. The syringe according to claim 22, wherein the barrel formation comprises a ratchet protrusion and the interspaced plunger formations comprise a series of complementary ratchet indents or the barrel formation comprises a ratchet indent and the interspaced plunger formations comprise a series of complementary ratchet protrusions.

24. The syringe according to claim 1, wherein the barrel formation comprises a locking mechanism to lock the syringe in the second state.

25. The syringe according to claim 17, wherein the barrel formation comprises a locking mechanism to lock the syringe in the second state.

26. The syringe according to claim 22, wherein the barrel formation comprises a locking mechanism to lock the syringe in the second state.

27. A syringe according to claim 22, wherein in the second state the barrel formation is spaced apart from the plunger.

\* \* \* \* \*